US007901914B2

(12) United States Patent
Tan et al.

(10) Patent No.: US 7,901,914 A0
(45) Date of Patent: Mar. 8, 2011

(54) MICROBIOLOGICAL METHOD OF THE BIOSYNTHESIS OF NATURAL BLUE-VIOLET COLORANTS VIOLACEIN AND DEOXYVIOLACEIN AND THE UTILIZATION THEREOF

(75) Inventors: Tjhing-Lok Tan, Langen (DE); Franz-Peter Montforts, Lilienthal (DE); Daniela Meyer, Bremen (DE)

(73) Assignee: Stiftung Alfred-Wegener-Institut fuer Polar- und Meeresforschung, Bremerhaven (DE)

( * ) Notice: Subject to any disclaimer, the term of this patent is extended or adjusted under 35 U.S.C. 154(b) by 1939 days.

(21) Appl. No.: 10/451,518

(22) PCT Filed: Dec. 20, 2001

(86) PCT No.: PCT/DE01/04900
§ 371 (c)(1),
(2), (4) Date: Jun. 20, 2003

(87) PCT Pub. No.: WO02/50299
PCT Pub. Date: Jun. 27, 2002

(65) Prior Publication Data
US 2004/0053375 A1 Mar. 18, 2004

(30) Foreign Application Priority Data
Dec. 20, 2000 (DE) .................................. 100 63 712

(51) Int. Cl.
*C12P 17/16* (2006.01)
(52) U.S. Cl. ........................................................ 435/118
(58) Field of Classification Search .................... 435/118
See application file for complete search history.

(56) References Cited

FOREIGN PATENT DOCUMENTS
DE 3935066 A 4/1991

OTHER PUBLICATIONS

Wille et al.: "A Short Synthesis of the Bacterial Pigments Violacein and Deoxyviolacein"; SYNTHESIS, Georg Thieme Verlag, STuttgart, Germany, No. 5, Apr. 12, 2001, pp. 759-762.
Patent Abstracts of Japan vol. 1999, No. 11, Sep. 30, 1999; JP 11-152687 National Institut of Sericultural and Entomological Science; Jun. 8, 1999; Abstract.
Patent Abstracts of Japan vol. 1998, No. 10, Aug. 31, 1998 JP 10-139612 A (Nakanihon Seni Kogyo Kyodo Kumiai) 26 Mai 1998; Abstract.
Patent Abstracts of Japan vol. 1998, No. 10, Aug. 31, 1998 JP 10-113169 A (Norin Suisansyo Sanshi Konchu Nogyo Gijutsu Kenkyusho; Kojima Atsushi) May 6, 1998; Abstract.
Database WPI, Section Ch, Week 199924 Derwent Publications Ltd., London, United Kingdom Class B02, AN 1999-278022 XP 002216054 BR 9 702 918 A (Unicamp Univ Estadual Campinas) May 4, 1999; Abstract.

Kiprianova E.A., et al.: Microorganisms of Pseudoalteromonas genus isolated from marine mussels; Inst. Microbiol. Virol. Natl. Acad. Sci. Ukr., 154 Zabolotny St., Kiev 252143; Mikrobiolohichinyi Zhurnal, 1996, vol. 58, No. 6, pp. 6-12.
Kawauchi Keiko et al.: A possible Immunosuppressant, cycloprodigiosin hydrochloride, obtained from pseudoalteromonas denitrificans Dep. Life Sci., Fac. Sci., Himaji Inst. Technol. Kanaji 1479-1, Kamigori, Ako-gun, Hyogo 678-12, Japan Piochemical and Biophysical Research Communications, 1997; vol. 237; No. 3; pp. 543-547.
Kim Hye-Sook et al.: Cycloprodigiosin hypochloride obtained from pseudoalteromonas denitrificans is a potent antimalarial agent. Dept. of Biochemistry, Faculty of Pharmaceutical Sciences, Okayama University, Tsushima-naka, Okayama, 700-8530, Japan Biological and Pharmceutical Bulletin, vol. 22, No. 5, pp. 532-534 ; May 1999.
Holmstrom, Carola et al.: Pseudoalteromonas—tunica sp. nov . . . , a bacterium that produces antifouling agents; International Journal of Systematic Bacteriology, Oct. 1998; vol. 48, No. 4, pp. 1205-1212.
Lovejoy Connie et al.: Algicidal effects of a novel marine pseudoalteromonas isolate (class Proteobacteria, gamma subdivision) on harmful algal bloom species of the genera Chattonella, Gymnodinium and Heterosigma; Applied and Environmental Microbiology, Aug. 1998; vol. 64, No. 8, pp. 2806-2813.
McCarthy, Susan A. et al.: Studies on Marine Purple Bacteria I. Production and Isolation of Purple Pigment by *Alteromonas luteoviolacea*; Nippon Suisan Gakkaishi (1985), 51(3), pp. 479-484.
Laatsch, Hartmut et al.: Spectroscopic Properties of Violacein and Related Compounds: Crystal Structure of Tetramethylviolacein; J.Chem.Soc., Perkin Trans. II (1984), pp. 1331-1339.
Hoshino, Tsumotu et al.: Biosynthesis of Violacein: A Novel Rearrangement in Tryptophan Metabolism with a 1.2 Shift of the Indole Ring; Agric. Biol. Chem. 51 (3) pp. 965-968 (1987).
Rettori, D. et al.: Production, Extraction and Purification of Violacein: An Antibiotic Pigment Produced by *Chromobacterium violaceum*; World Journal of Microbiology & Biotechnology 14, pp. 685-688 (1998).
Shirata, Akira: Isolation of Bacteria Producing Bluish-Purple Pigment and Use for Dyeing; JARQ 34, pp. 131-140 (2000).

*Primary Examiner* — L. Blaine Lankford
*Assistant Examiner* — Susan Hanley
(74) *Attorney, Agent, or Firm* — Karl Hormann

(57) ABSTRACT

Known microbiological methods are based upon the application of pigment-forming bacteria, in particular *Chromobacterium violaceum*. The yield of these methods is very low, however, so that large industrial applications are not possible. However, in many fields of industry, there exists a very great demand for natural blue dyes which are substantially suitable for human digestion, which cannot be satisfied at present. Therefore, the method in accordance with the invention is characterized by the application of the newly discovered marine sediment bacterium *Pseudoalteromonas* species of the "Black Beauty" strain (originally deposited under file number DSM 13623 with the Deutsche Sammlung von Mikroorganismen und Zellkulturen GmbH., Braunschweig, Germany pursuant to the Budapest Treaty on the International Recognition of the Deposit of Microorganisms for the Purposes of Patent Procedure). Compared to conventional methods, this marine sediment bacterium leads to an about thirteen-fold yield. An application of the natural dyes produced economically and by simple technical processes is thus possible in consumer and environmentally friendly products, in particular those from the food, textile or toy industries.

7 Claims, No Drawings

MICROBIOLOGICAL METHOD OF THE BIOSYNTHESIS OF NATURAL BLUE-VIOLET COLORANTS VIOLACEIN AND DEOXYVIOLACEIN AND THE UTILIZATION THEREOF

BACKGROUND OF THE INVENTION

1. Field of the Invention

The invention relates to a microbiological method for the biosynthesis of the natural blue-violet dyes violacein and deoxyviolacein from a pigment-forming bacterium by cultivation of the bacterium, removal of its cell mass by centrifuging, extraction of a raw dye extract from the cell mass and isolation of the dyes from the raw dye extract, and to the utilization of the dye produced by the microbiological method.

Dyes are of interest in more than one respect to microbiology and to chemistry. Since the ability to produce dyes is genetically fixed, the formation of dyes is also a first indication of the coincidental formation of antibiotic agents. Microbial pigments are of great structural diversity. They may be derivatives of the material classes of carotenoids, phenazine dyes, pyrrole dyes, azaquinones, etc.

2. The Prior Art

For about the past twenty years, there has been an ongoing search in the United States of America and in Japan, with thermophilic bacteria from deep sea vents and symbiontic bacteria from invertebrate and vertebrates, for biotechnologically useful bioactive natural substances. In countries of the European Community the usefulness of marine organisms has been recognized for the pharmaceutical industry, aqua culture, microbiological cleansing of oil contaminated areas of the ocean as well as for development processes of biological films and biological adhesion. However, in Germany it was not until three years ago that projects were conceived on a larger scale, which involve marine organisms in a more application-oriented direction of research. A large number of dyes are used in the textile, food, cosmetics and pharmaceutical industries. During recent years there has been a pronounced trend of consumers preferring products which contain natural substances. At present, yellow and red dyes are already being produced on an industrial scale from vegetable raw materials. However, in the mentioned industrial fields there exists a large demand for natural blue and violet dyes. The search for a dye from this spectrum has taken on a particular significance as a consequence of the legal prohibition against the use in foods of the red-blue dye monascine, isolated from *Monascus purpureus*. Classifying monascine as a food dye or colorant is not possible because of allergological problems. A microbiologically produced dye may thus help to close the gap and to open economically highly interesting paths.

Pigments from the blue-violet spectrum are formed, among others, by microorganisms. The azaquinone indigoidine is formed by several organisms (*Pseudonomas indigofera, Corynebacterium insidiosum, Arthrobacter arthrocyaneus* and *Arthrobacter polychromogenes*) and is secreted into the surrounding medium. This is of advantage in respect of a continuous process operation and of simplified product processing. It eliminates the step of cell pulping. Indigoidine has been officially approved as a food dye (E 132). Further approved food dyes from the blue dye spectrum are patent blue V (E 131), brilliant blue FCF and brilliant black (E 151). The absorption spectra of these compounds 11e in the range of 570 nm to 638 nm and are, therefore, particularly suitable for applications in food technology processes.

The blue-black pigment violacein, which is an indole derivative, was first described in literature in 1882. It was then that a violet dye was isolated from a bacterium which is now known as *Chromobacterium violaceum*. Heretofore, violacein could be isolated from the bacterial strains of *Janthinobacterium lividum, Chromobacterium lividum* and *Alteromanus luteoviolacea* (see H. Laatsch et al.: "Spectroscopic Properties of Violacein and Related Compounds: Crystal Structure of Tetramethylviolacein"; J. Chem. Soc. Perkin Trans 2., 1984, pp. 1331-1339). The structure of violacein was proved by synthesis in 1960. Chemically, violacein is characterized as 3-[1,2-dihydro-5-(5-hydroxy-1H-indole-3-yl)-2-oxo-3-H-pyrrole-3-ylidene]-1,3-dihydro-2H-indole-2-on, of the summation formula $C_{20}$—$H_{13}$—$N_3$—$O_3$ (molecular weight 343.33). The maximum absorption band, in a solution of methanol, is about 570 nm. In water, violacein is practically insoluble; but it is soluble in acetone, ethanol and dioxane. Violacein is the major component of a blue-violet pigment in *Chromobacterium violaceum* which is a microorganism taken from the soil and water of tropical regions, with deoxyviolacein occurring as a secondary component of identical structure, except that it has one less oxygen atom (summation formula $C_{20}$—$H_{13}$—$N_3$—$O_2$). So-called "native violacein" consists of a mixture of violacein with up to 10% deoxyviolacein. The violacein serves to protect the cell from radiation and to regulate the concentration of tryptophane below the toxic level. While violacein has antibiotic, antiviral and antitumoral properties, it displays no cyto-toxic or pathogenic effects. In more recent examinations, violacein has also been used for dying textiles. Good dying results have not only been obtained in connection with natural fibers such as silk, wool and cotton, but also with synthetic fibers such as polyamide (see Shirata et al.: "Isolation of Bacteria Producing Bluish-Purple Pigment and Use for Dying", Jpn. Agr. Res. Q 2000, 34(2), pp. 131-140, using pigment produced from *Janthinobacterium lividum*).

The biosynthesis from known microorganisms has been described in various publications. A method of producing native violacein, proceeding from the pigment-forming bacterium *Chromobacterium violaceum*, for use in the treatment of viral diseases, is described in German patent specification DE 3,935,066. The biosynthesis is based on the method steps of "cultivating the bacterium", "removing the cell mass by centrifuging", "extracting a raw dye extract from the cell mass", and "isolating the dye from the raw dye extract". The bacteria used as the starter material are cultivated on a solid or liquid nutrient. Preferably, the bacteria are cultivated in liquid nutrients since they can then be easily separated from their nutrient by centrifuging. The cultivation of the bacteria may be carried out with different process parameters in fermentation tanks. In the known method, the grown bacterial bed, after incubation, is separated and freeze-dried. Extraction of the raw violacein is carried out in methanol in a Soxhlet extractor. The methanol is removed by vacuum distillation. For isolating the violacein, the raw violacein is twice extracted by n-heptane, and is then filtered out. The residue is dissolved in a mixture of chloroform, acetone, pyridine 50:40:10. The mixture of the dye is then separated and purified by silica gel thin layer chromatography.

A simple method of obtaining highly purified violacein is known from the paper "Production, Extraction and Purification of Violacein: An Antibiotic Pigment Produced by *Chromobacterium violaceum* (Rettori, Duran, World Journal of Microbiology & Biotechnology 14 (1998), pp. 685-688. To cultivate the bacterium, non-sterile cotton rags are inoculated with a suspension culture of the pigment-forming *Chromobacterium violaceum* CCT 3496 and are stored in a strongly ventilated incubator where strong growth of the bacterium occurs. Thereafter, the cell mass is washed out of the cotton rags with a solvent, and is filtered to yield an extract of raw dye. A highly purified violacein is isolated from this as a dye by different methods (Soxhlet extractor, high-performance liquid chromatography). However, the yield is relatively low and lies in the range of milligrams per liter of nutrient.

The production of violacein from L-tryptophan as a biosynthetic starter material is known from the paper "Biosynthesis of Violacein: A Novel Rearrangement in Tryptophan Metabolism with 1,2-shift of the Indole Ring" (T. Hoshino et al., Agric. Biol. Chem. 51 (3), 1987, pp. 965-968, wherein the carbon skeleton of the pyrroleinone ring is formed by condensation of the side groups of two tryptophan molecules by a 1,2-shift of the indole ring. By comparison with the production of violacein from a pure suspension culture of *Chromobacterium violaceum* JCM 1249, it is possible to obtain an about 1.5-fold yield by adding L-tryptophan to the suspension culture. However, at the usual yield in the range of milligrams per liter of nutrient, this is still to be considered as a very low yield.

In summary, the known methods of biosynthesis of violacein and deoxyviolacein are not suitable for providing these dyes in greater quantities. For use in the pharmaceutical field this is not absolutely necessary, since in this context even the smallest quantities may be effectively applied. In other applications, however, the industrial demand for blue-violet dyes may be very large. If they are synthesized by the known methods, the use of large quantities of suspension cultures is necessary, the processing of which will be correspondingly demanding as regards equipment and time.

OBJECT OF THE INVENTION

It is thus an object of the present invention to provide a method of the kind described supra by which significantly larger yields of violacein and deoxyviolacein may be obtained economically and with simple process-related technological equipment than by known methods. This, in turn, is to make possible particular applications with larger dye quantities.

BRIEF SUMMARY OF THE INVENTION

In the accomplishment of this object, the microbiological method of the biosynthesis of the natural blue-violet violacein and deoxyviolacein dyes from a pigment-forming bacterium therefore provides for using the newly discovered marine sediment bacterium *Pseudoalteromonas* species of the "Black Beauty" strain, which was first deposited, in accordance with the Budapest Treaty on the International Recognition of the Deposit of Microorganisms for the Purposes of Patent Procedure, under file number DSM 13623 at the Deutsche Sammlung von Mikroorganismen und Zellkulturen GmbH., at Mascheroder Weg 1b, D-38124 Braunschweig, Germany (German Collection of Microorganisms and Cell Cultures GmbH. at Brunswick, Germany), which entails the occurrence of a yellow dye as an insignificant secondary product, which is separated by a further extraction of the raw dye extract by dichloromethane.

Advantageous improvements of the inventive method in respect of the individual method steps "cultivation of the bacterium", "removal of the cell mass by centrifuging", "extraction of the raw dye extract from the cell mass" and "isolating the dyes from the raw dye extract" may be gleaned from the sub-claims and from the ensuing specification. The blue-violet dyes violacein and deoxyviolacein whose biosynthesis in accordance with the invention is economical and is carried out by simple technological processes may be applied particularly advantageously to products of the food, textile, pharmaceutical or toy industries which friendly to consumers as well as to the environment.

DETAILED DESCRIPTION OF THE PREFERRED EMBODIMENT

A viable bacterium culture has been deposited at the International Depository DSMZ—Deutsche Sammlung von Mikroorganismen und Zellkulturen GmbH., at Mascheroder Weg 1b, D-38124 Braunschweig, Germany, in accordance with the Budapest Treaty on the International Recognition of the Deposit of Microorganisms for the Purposes of Patent Procedure. On 28 Jul. 2000 the applicant received from DSMZ a filing receipt of original deposit, issued in accordance with Rule 7.1, and a Certificate of Viability issued in accordance with Rule 10.2. Thus, under filing number DSM 13623, the applicant obtained protection for the newly discovered marine sediment bacterium Pseudoalteromonas species of the "Black Beauty" strain, and for its applications. With the present inventive method protection is claimed for the production off two blue-violet dyes using this sediment bacterium and for its use in industry (pigment and food industries) having a high demand for natural blue dyes. As far as is known to applicant, it is the first time that a marine microorganism has been used for such purposes. Hitherto, dyes from marine bacteria have seldom been examined, so that this constitute a larger potential for the chemistry of natural substances.

The possible yield of violacein from the marine sediment bacterium *Pseudoalteromonas* species of the "Black Beauty" strain is in the range of thirteen times higher than with Chromobacterium violaceum. For instance, from 38.97 g of moist mass of "Black Beauty" bacteria one obtains, after multiple extractions with hot methanol, a strongly violet colored solution from which, after removal of the solvent, 2.1 g of a jet black raw extract may be isolated. Compared to known methods, the yield factor by the inventive method which is based upon the biosynthesis of blue dyes from "Black Beauty", is very high. The marine sediment bacterium "Black Beauty" thus contains a very high proportion of pigment which renders it particularly suitable for the production of the native dyes violacein and deoxyviolacein. Moreover, the yield of pigment may yet be improved by optimizing the parameters at the various method steps (dwell time, solvent ratios, etc.), in particular during cultivation of the bacteria (nutrients, shaking frequency, oxygen charge, pH value, salt content, temperature, etc.). Overall the inventive method, at moderate process control and relatively low investment in time, results in great economic advantages, especially in respect of large scale technical uses. In this connection, it is particularly meaningful in view of the human-friendly characteristics of violacein to apply the biotechnically produced dyes in fields of industry having a large demand for environmentally friendly blue dyes, in particular in the food, toy and textile industries.

Thin-layer chromatographic tests show that the raw dye extract from the marine sediment bacterium "Black Beauty" is composed of three pigment fractions: a "weak" non-polar yellow dye, a further "weak" violet dye of low polarity, as well as a "very strong" polar dye of a deep violet color. The deep violet dye amounts to about 90% of the raw dye extract. An analytic examination of the structure by high-resolution mass spectrometry and multi-dimensional nuclear magnetic resonance spectroscopy has revealed that the deep violet dye is violacein and that the violet dye is deoxyviolacein. The main component of the yellow dye which appears in the raw dye extract as an insignificant secondary product with a share of 2%, is palmitoleic acid. This a fatty acid which is present as a subordinate secondary component in vegetable as well as animal fats and oils. However, the yellow dye is not the subject of the present invention and requires further examinations regarding its structure. In the context of the invention, it is significant that its proportion in the raw dye extract be very low, so that it does not noticeably lower the yield of blue-violet dyes, and that it be easily removable from the raw dye extract to facilitate the production therefrom of the two blue-violet dyes.

The individual steps of the method in accordance with the invention will hereafter be set forth with greater particularity in connection with exemplary embodiments. However, other variations of parameters as known from similar methods (see the cited state of the art, e.g. DE 3,8813,465) are possible as well since the individual method steps are of a general nature and are known to persons of average skill in the art, which is, in fact, the basis for the simplicity of the method.

Cultivation of the Bacteria

The starter culture for the synthesis of the bio mass was permanent bacteria culture found at the Borkum Watt and stored since 1985 at −80° C. at the Alfred-Wegener-Institut fuer Polar-und Meeresforschung, Bremerhaven, Germany. It was thawed and cultivated in a marine culture broth in four 2 liter Erlenmeyer flasks each container 1 liter of nutrient solution at 25° C. on a rotary shaker (100 to 110 rpm). After four days, the cells were harvested by centrifuging and the obtained cell mass was used for the extraction of dye.

Isolation of the Raw Extract 38.97 g of the bacterial cell mass (wet) is placed in an Erlenmeyer flask and converted to a slurry with about 250 ml of hot methanol. The mixture is left undisturbed for about 2 hours, until the cell have clearly precipitated. The supernatant is decanted, and the process is repeated several times, until the cells remain as a colorless grey mass. This mass may be used, for instance, as an additive to animal feed. The combined methanolic extracts is separated from the solvent in a rotary evaporator, and after drying in an oil pump vacuum, 2.10 g of a jet black raw extract is obtained.

Isolation of the Yellow Dye 514 mg of the raw extract are suspended in 50 ml of dichloromethane and stirred in the dark in an argon atmosphere for about one hour. The remaining solid residue (dye mixture) is separated, washed with dichloromethane and dried in an oil pump vacuum. After removal of the solvent 29.8 mg of a yellow-brown oily liquid is isolated from the mother liquor at the rotary evaporator. The liquid is column chromatographed over silica gel with dichloromethane/acetate 1+1. One obtains 10.2 mg of a yellow liquid which crystallizes when cold.

Isolation of the Two Blue-Violet Dyes 73.5 mg of the dye mixture separated from the yellow dye are suspended in 15 ml of dichloromethane/methanol (6+1) and left standing overnight. On the following morning the supernatant (13.5 mg) is chromatographed over 100 g silica gel with dichloromethane/methanol (6+1). One obtains 0.4 mg deoxyviolacein and 2.9 mg violacein. For analytical purposes, the latter may be additionally purified by preparative HPLC as well as by isothermal fractional crystallization from methanol/n-hexane.

The afore-mentioned steps of preparation and examination are part of the master's thesis "Isolation and Explanation of the Structure of Pigments from Marine Sediment Bacteria" (Diplomarbeit "Isolierung und Strukturaufklaerung von Pigmenten aus marinen Sedimentbakterien") which was presented to the Institute Administration for Organic Chemistry, Resort 2, of the University of Bremen, Germany. If required, further details regarding individual process and examination parameters and results may be taken from the thesis after its publication at the beginning of 2001. There also exists an application for support of the project during the time between 1 Apr. 2001 and 31 Mar. 2002 by the BMBF (German Federal Ministry for Education and Research), Biology, Energy, Environment (BEO) at the research center at Juelich, resort for ocean and polar research, geo sciences, relating to the subject "Research of Marine Native Substances—Application of native dyes from marine sediment bacteria". In this connection, participation by industrial partners is invited.

What is claimed is:

1. A microbiological method of the biosynthesis and isolation of natural blue-violet dyes violacein and oxyviolacein, comprising the steps of:
    providing a predetermined quantity of the marine sediment bacterium *Pseudoalteromonas* species of the "Black Beauty" strain DSM 13623, which produces said blue-violet dyes and a yellow dye occurring therein as an a secondary product;
    cultivating the bacterium on a nutrient broth to obtain a culture;
    centrifuging the culture to obtain a cell mass;
    extracting a raw dye extract comprising said blue-violet dyes and said yellow dye from the cell mass; and
    isolating said blue-violet dyes from the raw dye extract.

2. The method of claim 1, further comprising the step of extracting the yellow dye from the raw dye extract with dichloromethane.

3. The method of claim 1, wherein the step of extracting the raw dye extract from the cell mass further comprises the steps of:
    forming a slurry of the cell mass in methanol;
    precipitating the cell mass from said methanolic slurry for about 2 hours and separating the resultant supernatant which comprises a methanolic extract of the dye;
    repeating the steps of forming a slurry to separate said supernatant from the precipitated cell mass until the cell mass remains as a gray mass;
    removing solvents by subjecting the supernatant to a rotary evaporator to obtain a concentrated methanolic extract; and
    drying said concentrated methanolic extract in an oil pump vacuum.

4. The method of claim 2, wherein the step of removing the yellow dye is carried out in the dark in an argon atmosphere by stirring a suspension comprising the raw dye extract and dichloromethane causing the yellow fraction to dissolve and the blue-violet dyes to occur as a mixture of solids.

5. The method of claim 1, wherein the step of isolating the dyes from the raw dye extract further comprises the steps of:
    suspending the raw dye extract in a solvent mixture of 6 parts dichloromethane and 1 part methanol for about 12 hours to obtain a supernatant and a precipitate;
    decanting the supernatant; and
    subjecting the supernatant to column chromatography over silica gel with a mixture of 6 parts dichloromethane and 1 part methanol to obtain violacein.

6. The method of claim 5, further comprising the step of:
    subjecting said isolated violacein to high pressure chromatography to obtain purified violacein.

7. The method of claim 5, further comprising the step of:
    purifying the isolated violacein by isothermal recrystallization from a mixture of methanol and n-heptane.

* * * * *